(12) United States Patent
Brandewie et al.

(10) Patent No.: US 11,376,128 B2
(45) Date of Patent: Jul. 5, 2022

(54) ACETABULAR ORTHOPAEDIC PROSTHESIS AND METHOD

(71) Applicant: DePuy Ireland Unlimited Company, Ringaskiddy (IE)

(72) Inventors: Alena M. Brandewie, Warsaw, IN (US); Paul P. Lewis, Warsaw, IN (US); James A. Caywood, Warsaw, IN (US); Thomas P. Schmalzried, Rolling Hills, CA (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 395 days.

(21) Appl. No.: 16/236,801

(22) Filed: Dec. 31, 2018

(65) Prior Publication Data
US 2020/0205987 A1     Jul. 2, 2020

(51) Int. Cl.
*A61F 2/34*     (2006.01)
*A61F 2/36*     (2006.01)
*A61F 2/30*     (2006.01)

(52) U.S. Cl.
CPC .............. *A61F 2/34* (2013.01); *A61F 2/3607* (2013.01); *A61F 2/3662* (2013.01); *A61F 2002/30245* (2013.01); *A61F 2002/30428* (2013.01); *A61F 2002/342* (2013.01); *A61F 2002/365* (2013.01)

(58) Field of Classification Search
CPC ....................................... A61F 2/34; A61F 2/32
See application file for complete search history.

(56) References Cited

U.S. PATENT DOCUMENTS

| | | | |
|---|---|---|---|
| 3,707,006 A | 12/1972 | Bokros et al. |
| 3,801,989 A | 4/1974 | McKee |
| 3,818,514 A | 6/1974 | Clark |
| 3,829,904 A | 8/1974 | Ling et al. |
| 4,714,477 A | 12/1987 | Fichera et al. |
| 4,993,410 A | 2/1991 | Kimsey |
| 5,133,763 A | 7/1992 | Mullers |
| 5,133,765 A | 7/1992 | Cuilleron |
| 5,147,366 A | 9/1992 | Arroyo et al. |
| 5,156,626 A | 10/1992 | Broderick et al. |
| 5,405,394 A | 4/1995 | Davidson |
| 5,425,779 A | 6/1995 | Schlosser et al. |
| 5,458,649 A | 10/1995 | Spotorno et al. |
| 5,549,691 A | 8/1996 | Harwin |
| 5,569,263 A | 10/1996 | Hein |

(Continued)

FOREIGN PATENT DOCUMENTS

| | | |
|---|---|---|
| CN | 2580920 Y | 10/2003 |
| CN | 101883540 A | 11/2010 |

(Continued)

*Primary Examiner* — Jason-Dennis N Stewart
(74) *Attorney, Agent, or Firm* — Barnes & Thornburg LLP

(57) ABSTRACT

An orthopaedic components, prostheses, and methods for a hip arthroplasty are disclosed. The acetabular prosthetic component includes an outer rim and a cavity defined by an inner wall. The cavity is sized to receive a femoral head of a femoral prosthetic component. The inner wall includes a curved surface extending inwardly from the outer rim to an inner end, and a semi-spherical surface connected to the inner end of the curved surfac. The inner wall is shaped to resist dislocation of the femoral head component from the cavity and permit the femoral head component to articulate over a range of motion.

20 Claims, 4 Drawing Sheets

(56) References Cited

U.S. PATENT DOCUMENTS

| | | |
|---|---|---|
| 5,674,225 A | 10/1997 | Mueller |
| 5,735,905 A | 4/1998 | Parr |
| 5,865,850 A | 2/1999 | Matthews |
| 5,885,295 A | 3/1999 | McDaniel et al. |
| 5,888,211 A | 3/1999 | Sanders |
| 6,110,179 A | 8/2000 | Flivik et al. |
| 6,284,002 B1 | 9/2001 | Sotereanos |
| 6,344,060 B1 | 2/2002 | Schmotzer et al. |
| 6,488,713 B1 | 12/2002 | Hershberger |
| 6,585,771 B1 | 7/2003 | Buttermilch et al. |
| 7,179,297 B2 | 2/2007 | McLean |
| 7,192,449 B1 | 3/2007 | McQueen et al. |
| 7,819,925 B2 | 10/2010 | King et al. |
| 7,833,452 B2 | 11/2010 | Muratoglu et al. |
| 8,293,811 B2 | 10/2012 | Muratoglu et al. |
| 8,461,225 B2 | 6/2013 | Muratoglu et al. |
| 8,840,676 B2 | 9/2014 | Belew et al. |
| 8,858,645 B2 | 10/2014 | Grostefon et al. |
| 8,888,859 B2 | 11/2014 | Muratoglu et al. |
| 9,168,683 B2 | 10/2015 | Muratoglu et al. |
| 9,615,927 B2 | 4/2017 | Huff et al. |
| 9,724,201 B2 | 8/2017 | Grostefon et al. |
| 2001/0037156 A1 | 11/2001 | Burstein et al. |
| 2002/0052661 A1 | 5/2002 | Spotorno et al. |
| 2002/0193882 A1 | 12/2002 | Koller |
| 2003/0144742 A1 | 7/2003 | King et al. |
| 2004/0115172 A1 | 6/2004 | Bianchi et al. |
| 2004/0117029 A1 | 6/2004 | Lewis et al. |
| 2004/0199257 A1 | 10/2004 | Dooney |
| 2005/0143828 A1 | 6/2005 | Collins et al. |
| 2005/0146070 A1 | 7/2005 | Muratoglu et al. |
| 2007/0100464 A1 | 5/2007 | Meulink |
| 2007/0106389 A1* | 5/2007 | Croxton ............ A61F 2/32 623/22.17 |
| 2007/0118227 A1 | 5/2007 | King et al. |
| 2007/0250175 A1 | 10/2007 | Meridew et al. |
| 2008/0215142 A1 | 9/2008 | Muratoglu et al. |
| 2009/0036993 A1 | 2/2009 | Metzger |
| 2010/0082101 A1 | 4/2010 | Muratoglu et al. |
| 2010/0131073 A1 | 5/2010 | Meridew et al. |
| 2010/0241239 A1 | 9/2010 | Smith |
| 2011/0247229 A1 | 10/2011 | Anapliotis et al. |
| 2012/0089235 A1 | 4/2012 | Conway et al. |
| 2012/0185059 A1 | 7/2012 | Vankoski et al. |
| 2012/0319332 A1 | 12/2012 | Mcminn |
| 2013/0060344 A1 | 3/2013 | Pierce |
| 2013/0204389 A1 | 8/2013 | Kumar et al. |
| 2013/0245775 A1 | 9/2013 | Metcalfe |
| 2013/0325139 A1 | 12/2013 | Steiner et al. |
| 2016/0074167 A1 | 3/2016 | Vautrin |

FOREIGN PATENT DOCUMENTS

| | | |
|---|---|---|
| CN | 102458311 A | 5/2012 |
| DE | 10335442 A1 | 2/2005 |
| DE | 102008030260 A1 | 12/2009 |
| EP | 0207873 A1 | 1/1987 |
| EP | 0342014 A1 | 11/1989 |
| EP | 0663194 A1 | 7/1995 |
| EP | 0807426 A2 | 11/1997 |
| EP | 1293179 A1 | 3/2003 |
| EP | 1359950 A1 | 11/2003 |
| EP | 1223895 B1 | 12/2006 |
| EP | 1091705 B1 | 8/2007 |
| EP | 1825834 A1 | 8/2007 |
| EP | 2198808 A1 | 6/2010 |
| EP | 1841686 B1 | 2/2012 |
| EP | 2574310 A2 | 4/2013 |
| FR | 1481424 A | 5/1967 |
| FR | 2105998 A5 | 4/1972 |
| GB | 1485295 A | 9/1977 |
| GB | 2042897 A | 10/1980 |
| GB | 2152385 A | 8/1985 |
| JP | 11155890 A | 6/1999 |
| JP | 3172112 B2 | 6/2001 |
| JP | 2002345858 A | 12/2002 |
| JP | 2003175061 A | 6/2003 |
| JP | 4051950 B2 | 2/2008 |
| JP | 6007386 B2 | 10/2016 |
| RU | 2309706 C2 | 11/2007 |
| WO | 9522944 A1 | 8/1995 |
| WO | 03049649 A1 | 6/2003 |
| WO | 2004069096 A2 | 8/2004 |
| WO | 2008117056 A1 | 10/2008 |
| WO | 2009106867 A1 | 9/2009 |
| WO | 2010129880 A2 | 11/2010 |
| WO | 2012035294 A2 | 3/2012 |
| WO | 2016200735 A1 | 12/2016 |
| WO | 2017003570 A1 | 1/2017 |
| WO | 2017053183 A1 | 3/2017 |

* cited by examiner

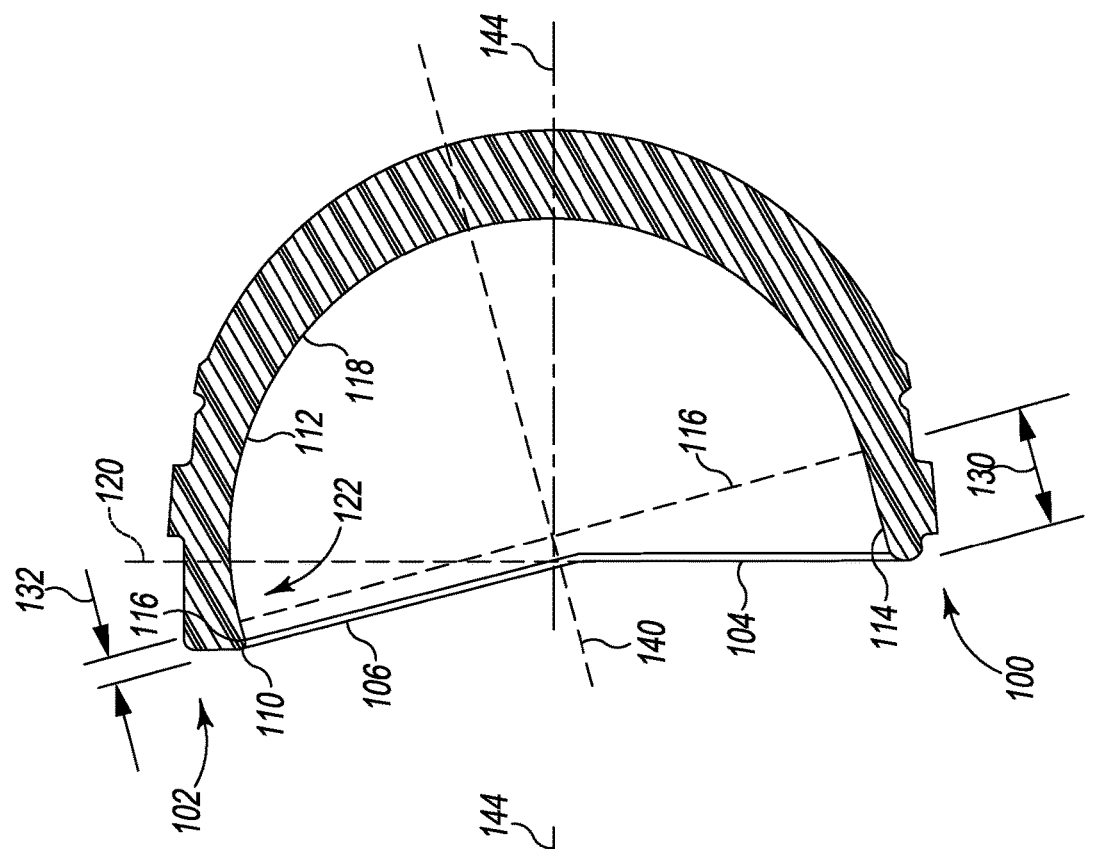
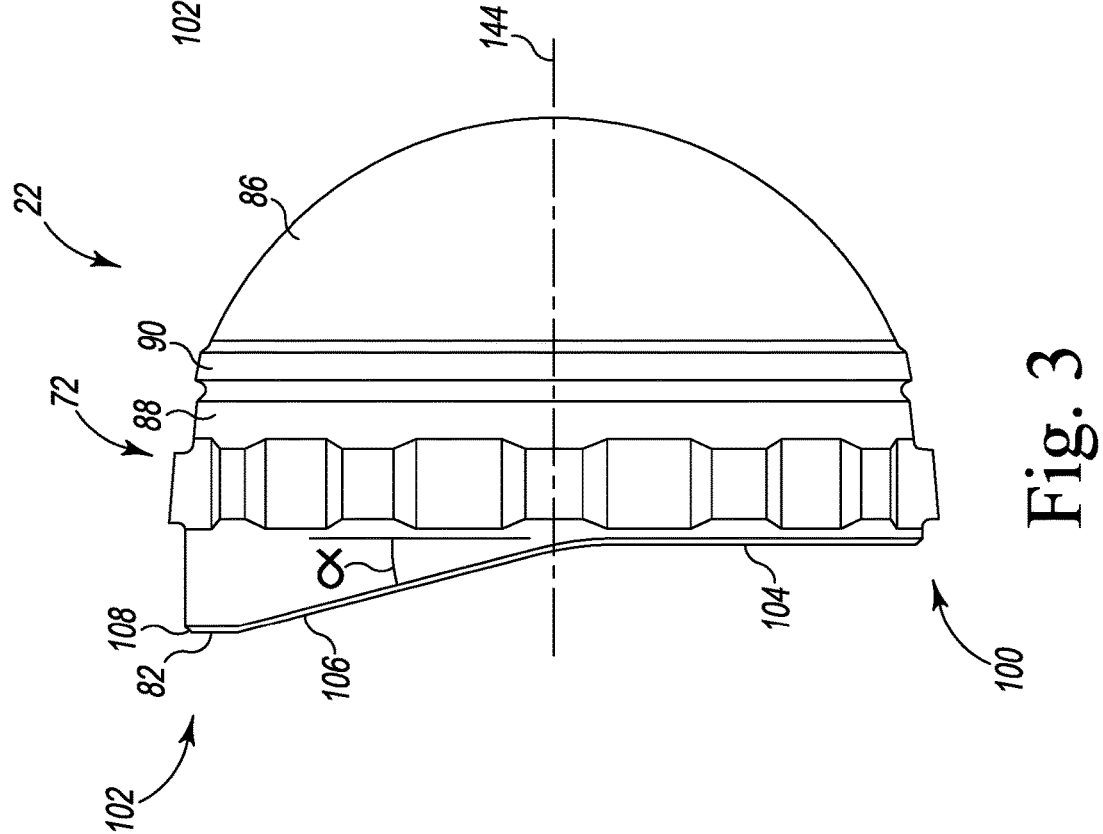

ACETABULAR ORTHOPAEDIC PROSTHESIS AND METHOD

TECHNICAL FIELD

The present disclosure relates generally to orthopaedic prosthetic components and, more particularly, to acetabular prosthetic components.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or insert coupled to the shell and configured to engage the femoral head. The femoral head prosthetic component and inner insert of the acetabular component form a ball and socket joint that approximates the natural hip joint.

SUMMARY

According to one aspect of the disclosure, an orthopaedic prosthesis for use in a hip arthroplasty surgical procedure is disclosed. The orthopaedic prosthesis includes an acetabular prosthetic component that has a cavity sized to receive a femoral head of a femoral prosthetic component. The cavity is defined by an inner wall that is shaped to resist dislocation of the femoral head of the femoral prosthetic component. In some embodiments, the inner wall of the acetabular prosthetic component may include a cylindrical surface extending inwardly from an outer rim of the acetabular prosthetic component to an inner end and a semi-spherical surface connected to the inner end of the cylindrical surface. In some embodiments, the cavity may be sized such that a geometric center of the femoral prosthetic component is positioned lateral of the outer rim of the acetabular prosthetic component when received in the cavity.

According to another aspect, an orthopaedic prosthetic component is disclosed. The orthopaedic prosthetic component comprises an acetabular prosthetic component including an outer rim, an inner wall extending inwardly from the outer rim, and a cavity defined by the inner wall. The cavity is sized to receive a femoral head of a femoral prosthetic component. The inner wall includes a cylindrical surface extending inwardly from the outer rim to an inner end, and a semi-spherical surface connected to the inner end of the cylindrical surface. When the acetabular prosthetic component is viewed in cross-section, the cylindrical surface extends a first distance from the outer rim to the inner end on an inferior side of the acetabular prosthetic component and the cylindrical surface extends a second distance from the outer rim to the inner end on a superior side of the acetabular prosthetic component. The second distance is less than the first distance.

In some embodiments, the outer rim may include an inferior rim section and a superior rim section that extends at a non-orthogonal angle relative to the inferior rim section. In some embodiments, the non-orthogonal angle may be equal to about 15 degrees.

In some embodiments, the inferior rim section may be positioned in an imaginary plane, and the inner end of the cylindrical surface on the superior side of the acetabular prosthetic component may be positioned lateral of the imaginary plane such that a portion of the semi-spherical surface extends through the imaginary plane. The portion of the semi-spherical surface may define a cupped region that resists dislocation of the femoral head component from within the cavity.

In some embodiments, the acetabular prosthetic component may include an outer wall that is positioned opposite the inner wall. The outer wall may include a lateral edge that is positioned lateral of the imaginary plane.

In some embodiments, the acetabular prosthetic component may include a component axis that extends orthogonal to the inferior rim section, and the semi-spherical surface may include a central axis that extends at a non-orthogonal angle relative to the component axis. Additionally, in some embodiments, the non-orthogonal angle may be equal to about 15 degrees.

In some embodiments, the cylindrical surface may include a second central axis that is coincident with the central axis of the semi-spherical surface.

Additionally, in some embodiments, the orthopaedic prosthetic component may also comprises a prosthetic shell including an outer surface shaped to be positioned in a surgically-prepared acetabulum of a patient's pelvis and an inner cavity that receives the acetabular prosthetic component.

In some embodiments, the prosthetic shell may include a second central axis that is coincident with the component axis of the acetabular prosthetic component.

According to another aspect, an orthopaedic prosthesis is disclosed. The orthopaedic prosthesis comprises an acetabular shell component having a distal rim and a concave curved surface extending from the distal rim to define an inner cavity. The distal rim is positioned in an imaginary plane. The orthopaedic prosthesis also comprises an insert component configured to be received in the inner cavity. The insert component includes an outer rim, an inner wall extending inwardly from the outer rim, and a cavity that is defined by the inner wall and is sized to receive a femoral head of a femoral prosthetic component. The inner wall includes a cylindrical surface and a semi-spherical surface, and the semi-spherical surface extends through the imaginary plane to a superior edge that is positioned lateral of the imaginary plane. The superior edge may define a region shaped to resist dislocation and separation of the femoral head of the femoral prosthetic component from the insert component.

In some embodiments, the acetabular shell component may include a shell axis that extends orthogonal to the imaginary plane, and the cylindrical surface may include a first central axis and the semi-spherical surface includes a second central axis that extends coincident with the first central axis. When the orthopaedic prosthesis is viewed in cross-section, a non-orthogonal angle may be defined between the coincident first and second central axis and the shell axis. In some embodiments, the non-orthogonal angle may be equal to about 15 degrees.

In some embodiments, the outer rim of the insert component may include an inferior rim section and a superior rim section that extends at a non-orthogonal angle relative to the inferior rim section. Additionally, in some embodiments, the inferior rim section of the insert component may extend parallel to the distal rim of the acetabular shell component.

In some embodiments, the insert component may include an outer wall that is positioned opposite the inner wall. The outer wall may include a lateral edge that is positioned lateral of the imaginary plane.

In some embodiments, the orthopaedic prosthesis may further comprises the femoral prosthetic component including an elongated stem and the femoral head secured to the elongated stem. Additionally, in some embodiments, the femoral head may include a geometric center that is positioned lateral of the imaginary plane of the shell component.

In some embodiments, when the orthopaedic prosthesis is viewed in cross-section, the cylindrical surface may extend a first distance from the outer rim to the inner end on an inferior side of the insert component and the cylindrical surface may extend a second distance from the outer rim to the inner end on a superior side of the insert component. The second distance may be less than the first distance. The cylindrical surface may define a bore having a superior side that has a depth that is less than a depth of its inferior side.

According to another aspect, an orthopaedic prosthesis comprises a femoral prosthetic component including an elongated stem and a femoral head secured to the elongated stem and an acetabular shell component having a distal rim and a concave curved surface extending from the distal rim to define an inner cavity. The distal rim is positioned in an imaginary plane. The orthopaedic prosthesis also comprises an insert component configured to be received in the inner cavity. The insert component includes an outer rim, an inner wall extending inwardly from the outer rim, and a cavity defined by the inner wall. The cavity is sized to receive the femoral head of the femoral prosthetic component. The inner wall includes a cylindrical surface extending inwardly from the outer rim to an inner end, and a semi-spherical surface connected to the inner end of the cylindrical surface. The semi-spherical surface extends through the imaginary plane to define a region shaped to resist dislocation of the femoral head, and the femoral head includes a geometric center that is positioned lateral of the imaginary plane of the shell component.

According to another aspect, a method is disclosed. The method comprises aligning an insert component with a distal cavity of an acetabular shell component, rotating the insert component to position a first rim section of the insert component superior of a second rim section of the insert component, and securing the insert component to the acetabular shell component. The second rim section of the insert component extends parallel to a distal rim of the acetabular shell component. The insert component includes a semi-spherical inner surface that has a superior sedge that extends through an imaginary plane defined by the distal rim of the acetabular shell component when the insert component is secured to the acetabular shell component.

In some embodiments, the method may further comprise advancing a femoral head component into engagement with the semi-spherical inner surface of the insert component to seat the femoral head component in the insert component. When the femoral head component is seated in the insert component, a geometric center of the femoral head component is positioned lateral of the imaginary plane of the acetabular shell component.

In some embodiments, the step of securing the insert component to the acetabular shell component may comprise advancing a rib formed on one of the insert component and the acetabular shell component into a groove of the other of the insert component and the acetabular shell component.

BRIEF DESCRIPTION OF THE DRAWINGS

The detailed description particularly refers to the following figures, in which:

FIG. 3 is a side elevation view of an insert component of the acetabular prosthesis of FIG. 2;

FIG. 4 is a cross-sectional elevation view of the insert component taken along the line 4-4 in FIG. 2.

DETAILED DESCRIPTION OF THE DRAWINGS

Figure 1:
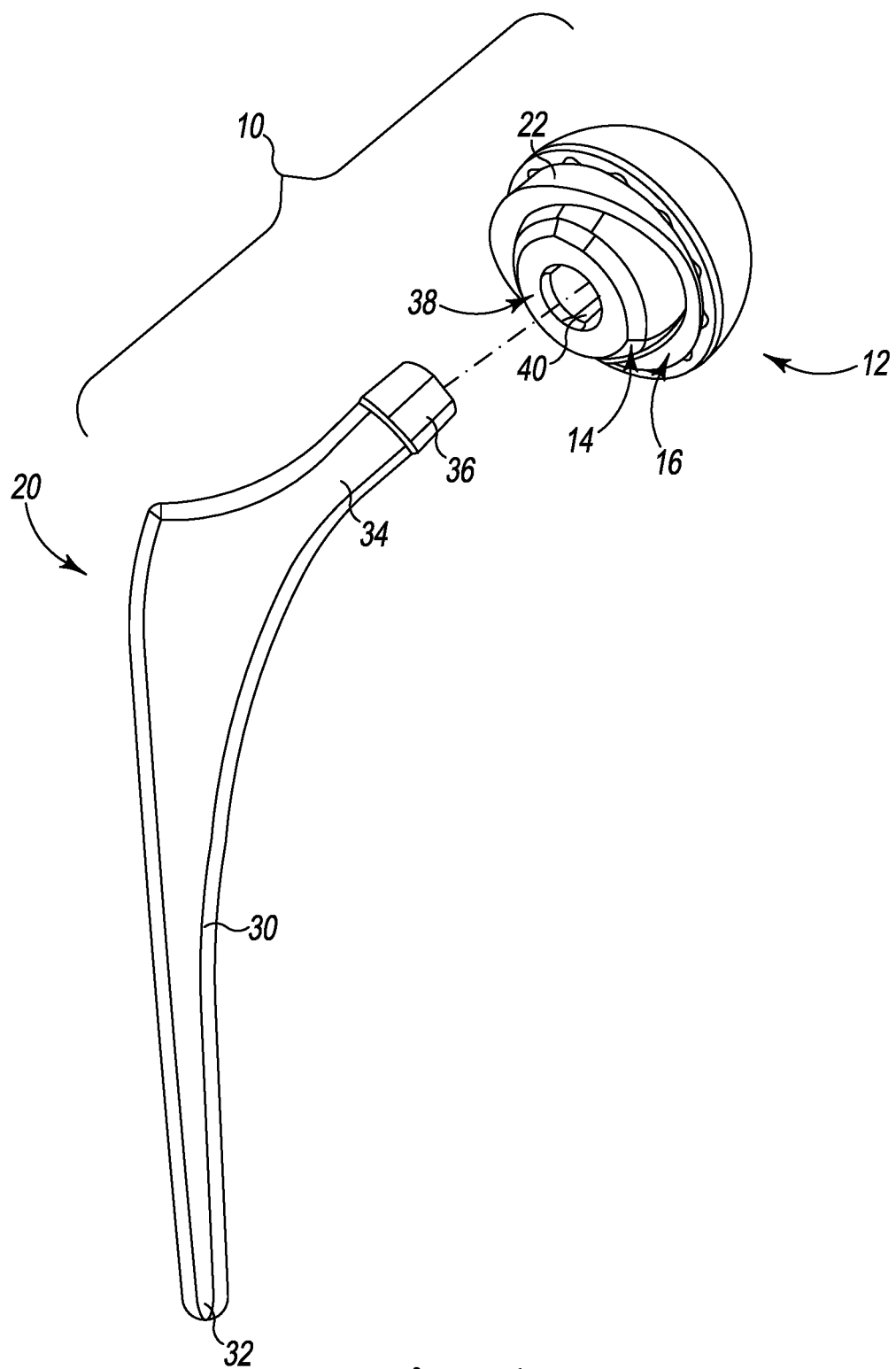
FIG. 1 is a perspective view of an orthopaedic prosthesis for use in a hip arthroplasty.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, a hip orthopaedic prosthesis assembly 10 includes a plurality of components, including an acetabular prosthesis 12 that is sized to be implanted in a surgically-prepared acetabulum of a patient's pelvis. The assembly 10 also includes a femoral head component 14 that is received in a cavity 16 defined in the acetabular prosthesis 12. The prosthesis assembly 10 also includes a femoral stem component 20 that is configured to be secured to the femoral head component 14 to form a femoral prosthetic component. As described in greater detail below, the acetabular prosthesis 12 includes an insert component 22 that is shaped to support and stabilize the femoral head 14 over the range of motion of the prosthesis assembly 10.

In the illustrative embodiment, the femoral stem component 20 includes an elongated body 30 that extends from a distal tip 32. The stem component 20 is sized and shaped to be implanted in a surgically-prepared proximal end of a patient's femur. The stem component 20 also includes a neck 34 that extends superiorly and immediately from the elongated body 30 to a tapered trunnion 36. The tapered trunnion 36 is sized to be positioned in a distal bore 38 defined in the femoral head component 14. The bore 38 is defined by a tapered inner surface 40 that is configured to engage the tapered trunnion 36 to secure the head component 14 to the stem component 20. The femoral head component 14 and the femoral stem component 20 are separately formed from implant-grade metallic materials such as, for example, titanium.

Figure 2:
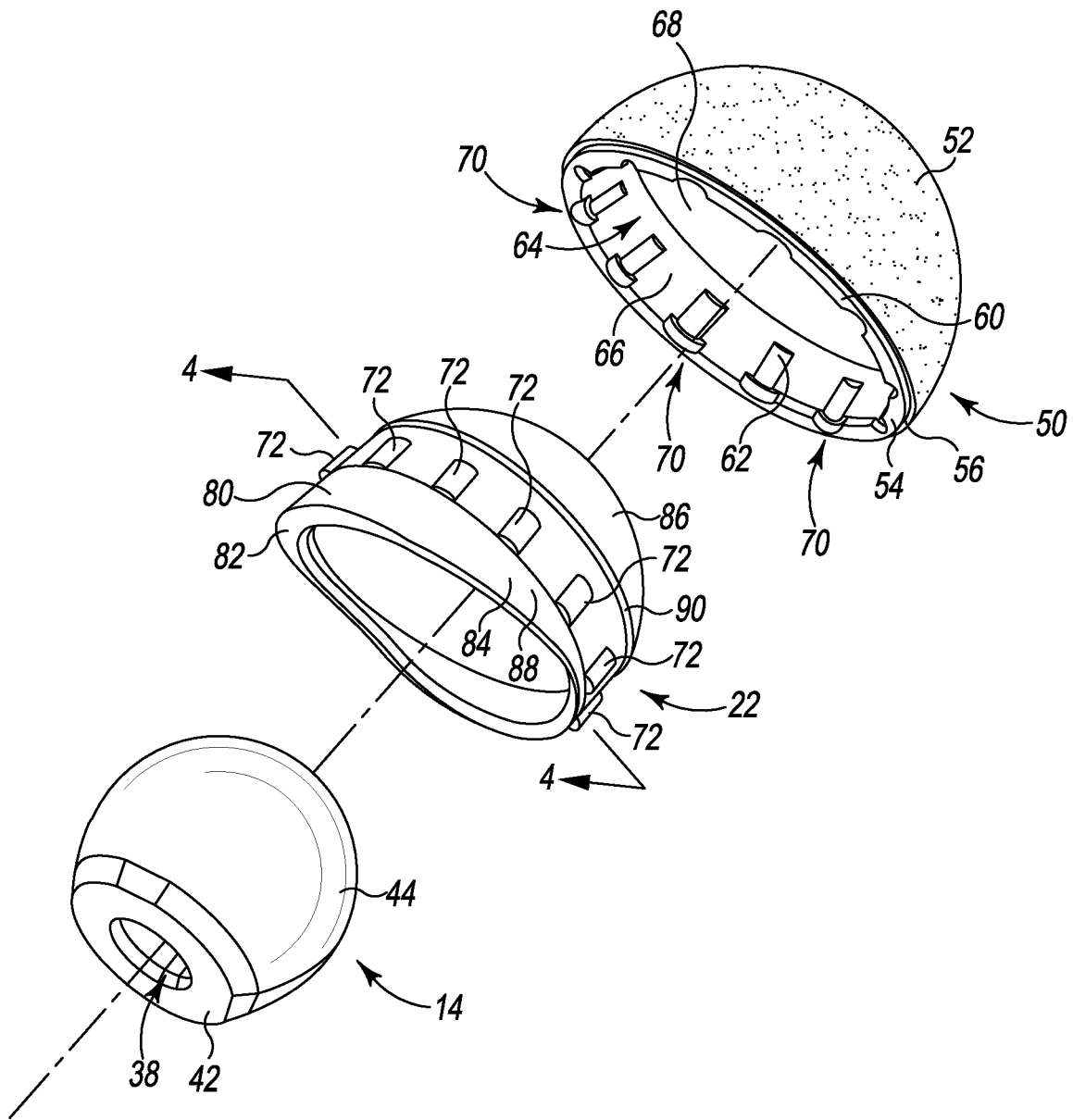
FIG. 2 is an exploded perspective view of an acetabular prosthesis and a femoral head component of the orthopaedic prosthesis.

Referring now to FIG. 2, the bore 38 of the femoral head component 14 is defined in a distal surface 42. The head component 14 also includes a convex curved surface 44 that is connected to, and extends from, the distal surface 42. In the illustrative embodiment, the convex curved surface 44 is a semi-spherical surface that is shaped to be received in the cavity 16 of the acetabular prosthesis 12.

As described above, the acetabular prosthesis 12 includes an insert component 22, which is configured to be coupled to a shell component 50 of the acetabular prosthesis 12. The insert component 22 is illustratively formed from a polymeric material such as, for example, polyethylene. The shell component 50, is separately formed from implant-grade metallic materials such as, for example, titanium. The shell component 50 also includes a Porocoat® outer coating 52 that permits bone to affix biologically to the shell component 50 after implantation. It should be appreciated that in other embodiments the Porocoat® outer coating may be omitted.

The shell component 50 has a distal rim 54 and an outer wall 56 that extends from the distal rim 54. The outer wall 56 includes a convex curved outer surface and an annular outer surface 60 that extends from the distal rim 54 to the curved outer surface. In the illustrative embodiment, the convex curved outer surface is semi-spherical and shaped to match the shape of a patient's surgical prepared acetabulum. The Porocoat® outer coating 52 covers the outer surface and follows its geometric shape.

An inner wall 62 extends inwardly from the distal rim 54 to define a cavity 64 in the shell component 50 that is sized to receive the insert component 22. The inner wall 62 includes an annular inner surface 66 that is positioned opposite the annular outer surface 60 and a concave curved inner surface 68 that is connected to the annular inner surface 66. A plurality of slots 70, which extend inwardly form the distal rim 54, are defined in the inner wall 62. The slots 70 are spaced apart around the circumference of the distal rim 54 and are shaped to receive corresponding keys 72 of the insert component 22, as described in greater detail below.

The insert component 22 includes a body 80 that is shaped to be received in the cavity 64 of the shell component 50. The body 80 includes an outer rim 82 and an outer wall 84 that extends from the outer rim 82. The outer wall 84 includes a convex curved outer surface 86 and an annular outer surface 88 that extends from the outer rim 82 to the curved outer surface 86. The keys 72 extend outwardly from, and are positioned around the outer circumference of, the annular outer surface 88. The insert component 22 also includes an annular rib 90 that is formed on the convex curved outer surface 86 and is sized to be received in a corresponding annular slot 92 (see FIG. 5) formed in the concave curved inner surface 68 of the shell component 50. The rib 90 engages the shell component 50 to secure the insert component 22 to the shell component 50. It should be appreciated that in other embodiments the rib may be included on the shell component and the slot on the insert component.

Referring now to FIG. 3, the insert component 22 has a side 100 that is positioned inferiorly when the acetabular prosthesis 12 is placed at in the proper orientation in a patient's acetabulum and another side 102 that is positioned superiorly. The outer rim 82 includes a rim section 104 that is positioned on the inferior side 100 of the insert component 22 and another rim section 106 that is connected to the rim section 104 and extends to the superior side 102 of the insert component 22. As shown in FIG. 3, the superior rim section 106 is connected to a lateral edge 108 of the outer wall 84 of the insert component 22.

When the insert component 22 is coupled to the shell component 50, the inferior rim section 104 extends parallel to the distal rim 54 of the shell component 50. The superior rim section 106 is sloped relative to the inferior rim section 104 such that an angle α is defined between the sections 104, 106. The angle α is a non-orthogonal angle that is greater than 90 degrees. In the illustrative embodiment, the angle α is equal to about 15 degrees. It should be appreciated that the term "about" as used herein denotes a range of ±2% or less of the base number. As such, "about 15 degrees" may be understood as a range including±2% of 15 degrees. It should also be appreciated that in other embodiments the angle α may be in a range of about 15 to about 30 degrees.

As described above, the acetabular prosthesis 12 includes a cavity 16 that is sized to receive the femoral head component 14. The cavity 16 has an opening 110 that is defined by the outer rim 82 of the insert component 22. As shown in FIG. 4, the insert component 22 includes an inner wall 112 that extends inwardly from the outer rim 82 to define the cavity 16. The inner wall 112 includes a curved surface 114 that extends from the outer rim 82 to an inner end 116 (partially indicated by the broken line in FIG. 4). The inner wall 112 also includes a semi-spherical surface 118 that is connected to the inner end 116 of the curved surface 114. The semi-spherical surface 118 is a concave curved surface that is shaped to match the semi-spherical convex surface 44 of the femoral head component 14. In use, the femoral head component 14 articulates on the semi-spherical surface 118 of the insert component 22.

As shown in FIG. 4, the inferior rim section 104 is positioned in an imaginary plane 120 that extends through the inner wall 112. The semi-spherical surface 118 extends through the imaginary plane 120 on the superior side 102 of the insert component 22 to define a cupped superior region 122 that resists dislocation of the femoral head component 14 from the cavity 16 and thereby contributes to the retention of the femoral head component 14 in the cavity 16. The semi-spherical surface 118 connects to the inner end 116 on the superior side 102 along a line that is lateral of the imaginary plane 120.

In the illustrative embodiment, the curved surface 114 is a cylindrical surface to define a distal bore. When viewed in cross-section as shown in FIG. 4, the cylindrical surface 114 extends a distance 130 on the inferior side 100 of the insert component 22 and extends a distance 132 on the superior side 102 of the insert component 22. The distance 132 is less than the distance 130 such that the superior depth of the distal bore is less than the inferior depth of the bore. The cylindrical surface 114 has a central axis 140 that extends coincidently with a central axis 142 of the semi-spherical surface 118.

Figure 5:
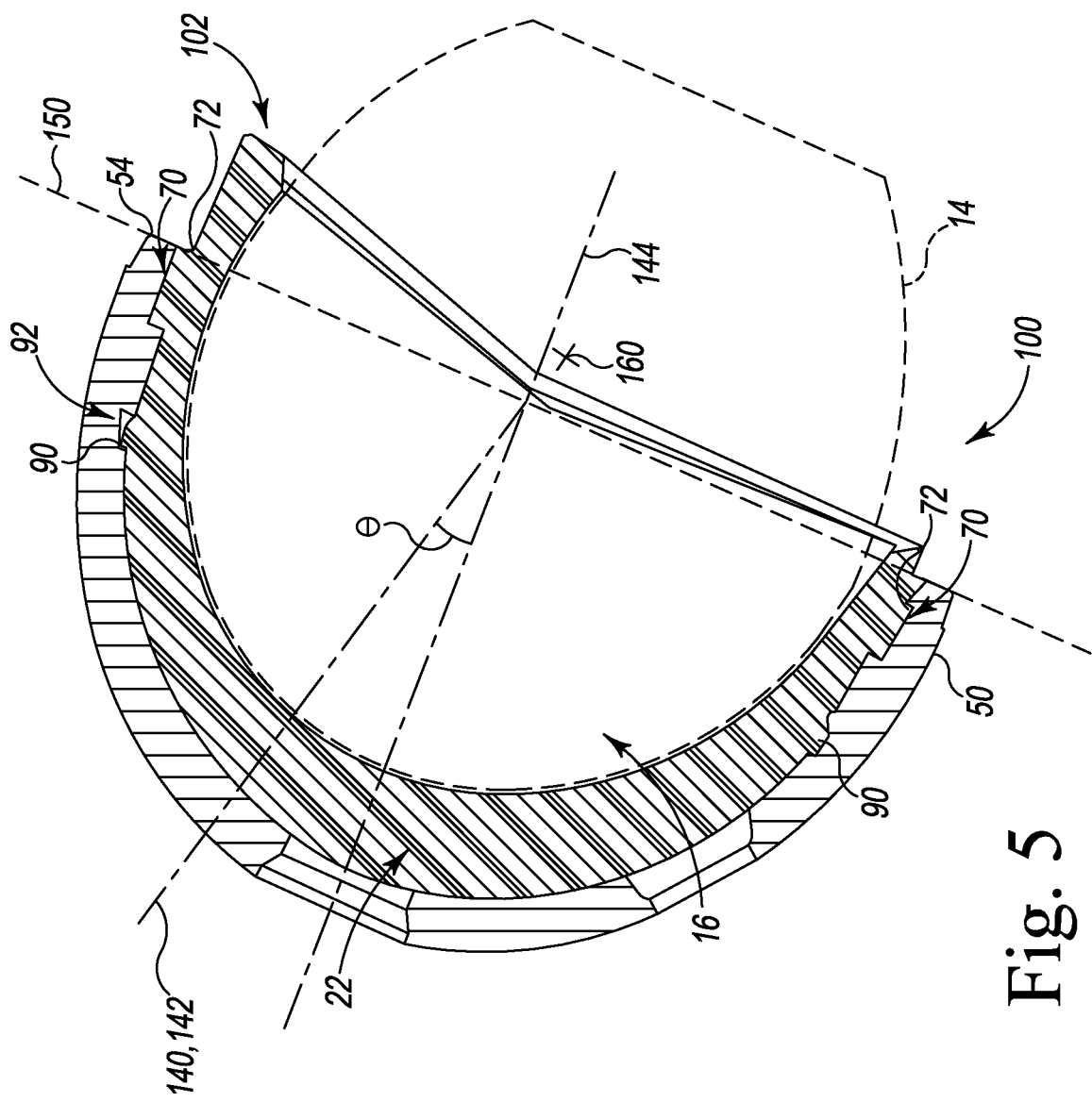
FIG. 5 is a cross-sectional elevation view similar to FIG. 4 with the insert component coupled to a prosthetic shell component of the acetabular prosthesis of FIG. 2.

Referring now to FIG. 5, the shell component 50 has a central axis 144. When the insert component 22 is coupled to the shell component 50, the central axis 144 extends at an angle θ relative to the axes 140, 142. In the illustrative embodiment, the angle θ is equal to about 15 degrees. It should be appreciated that in other embodiments the angle θ may be in a range of about 15 to about 30 degrees.

The distal rim 54 of the shell component 50 is positioned in an imaginary plane 150 that extends parallel to the imaginary plane 120 in which the inferior section 104 of the insert component 22 is positioned. As shown in FIG. 5, the superior side 102 of the insert component 22 extends through the imaginary plane 150 such that the lateral edge 108 of the outer wall 84 on that side of the insert component 22 is positioned lateral of the imaginary plane 150.

The femoral head component 14 has a geometric center 160 in the illustrative embodiment. As shown in FIG. 5, the cavity 16 is sized such that the geometric center 160 is positioned lateral of the imaginary plane 150 when the femoral head component 14 is properly seated in the cavity 16. In that way, the position of the femoral head component 14 is lateralized to permit a greater range of motion for the femoral components 14, 20 relative to the acetabular prosthesis 12.

In use, a surgeon may surgically prepare the patient's natural acetabulum to receive an acetabular prosthesis 12. To do so, the surgeon may utilize a surgical reamer to prepare the patient's bone to receive the prosthesis 12. The surgeon may also utilize one or more surgical trial components to determine which prosthesis is appropriate for the patient. For example, it should be appreciated that the surgeon may select an appropriately-sized shell component 50 and insert component 22 from a number of shell components and insert components of different sizes. The surgeon may insert the shell component 50 into the patient's surgically-prepared acetabulum, advancing the shell component 50 into engagement with the concave bone surface defining the acetabulum. When the shell component 50 is oriented at a desired anteversion and inclination, the surgeon may secure the shell component 50 to the patient's bone.

To assemble the prosthesis 12, the surgeon may align the selected insert component 22 with the cavity 64 defined in the shell component 50 and advance the insert component 22 along the axis 144 to position the convex curved outer surface 86 of the insert component 22 in the cavity 64. The surgeon may rotate the insert component 22 about the axis 144 to align the keys 72 with the slots 70 defined in the shell component 50 and place the rim section 106 of the insert component 22 superior to the rim section 104. Once properly aligned, the surgeon may advance the keys 72 into the slots 70 and engage the rib 90 of the insert component 22 with the slot 92 of the shell component 50 to couple the insert component 22 to the shell component 50.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic prosthetic component, comprising:
an acetabular prosthetic component configured to be received in a prosthetic shell, the acetabular prosthetic component including an outer rim, an inner wall extending inwardly from the outer rim, and a cavity defined by the inner wall, the cavity being sized to receive a femoral head of a femoral prosthetic component,
wherein the inner wall includes a cylindrical surface extending inwardly from the outer rim to an inner end, and a semi-spherical surface connected to the inner end of the cylindrical surface,
wherein, when the acetabular prosthetic component is viewed in cross-section, the cylindrical surface extends a first distance from the outer rim to the inner end on an inferior side of the acetabular prosthetic component and the cylindrical surface extends a second distance from the outer rim to the inner end on a superior side of the acetabular prosthetic component, the second distance being less than the first distance, and
wherein the outer rim includes an inferior rim section that is positioned in an imaginary plane such that a portion of the semi-spherical surface on the superior side extends through the imaginary plane.

2. The orthopaedic prosthetic component of claim 1, wherein the outer rim includes a superior rim section that extends at a non-orthogonal angle relative to the inferior rim section.

3. The orthopaedic prosthetic component of claim 2, wherein:
the acetabular prosthetic component includes a component axis that extends orthogonal to the inferior rim section, and
the semi-spherical surface includes a central axis that extends at a non-orthogonal angle relative to the component axis.

4. The orthopaedic prosthetic component of claim 3, wherein the non-orthogonal angle is equal to about 15 degrees.

5. The orthopaedic prosthetic component of claim 3, wherein the cylindrical surface includes a second central axis that is coincident with the central axis of the semi-spherical surface.

6. The orthopaedic prosthetic component of claim 3, further comprising the prosthetic shell including an outer surface shaped to be positioned in a surgically-prepared acetabulum of a patient's pelvis and an inner cavity that receives the acetabular prosthetic component.

7. The orthopaedic prosthetic component of claim 6, wherein the prosthetic shell includes a second central axis that is coincident with the component axis of the acetabular prosthetic component.

8. The orthopaedic prosthetic component of claim 2, the inner end of the cylindrical surface on the superior side of the acetabular prosthetic component is positioned lateral of the imaginary plane such that the portion of the semi-spherical surface extends through the imaginary plane.

9. The orthopaedic prosthetic component of claim 8, wherein the acetabular prosthetic component includes an outer wall that is positioned opposite the inner wall, the outer wall including a lateral edge that is positioned lateral of the imaginary plane.

10. The orthopaedic prosthetic component of claim 1, wherein the non-orthogonal angle is equal to about 15 degrees.

11. An orthopaedic prosthesis, comprising:
an acetabular shell component having a distal rim and a concave curved surface extending from the distal rim to define an inner cavity, the distal rim being positioned in an imaginary plane, and
an insert component configured to be received in the inner cavity, the insert component including an outer rim, an inner wall extending inwardly from the outer rim, and a cavity that is defined by the inner wall and is sized to receive a femoral head of a femoral prosthetic component,
wherein the inner wall includes a cylindrical surface and a semi-spherical surface, and wherein the semi-spherical surface extends through the imaginary plane to a superior edge that is positioned lateral of the imaginary plane.

12. The orthopaedic prosthesis of claim 11, wherein:
the acetabular shell component includes a shell axis that extends orthogonal to the imaginary plane,
the cylindrical surface includes a first central axis and the semi-spherical surface includes a second central axis that extends coincident with the first central axis, and
when the orthopaedic prosthesis is viewed in cross-section, a non-orthogonal angle is defined between the shell axis and the coincident first and second central axes.

13. The orthopaedic prosthesis of claim 12, wherein the non-orthogonal angle is equal to about 15 degrees.

14. The orthopaedic prosthesis of claim 11, wherein the outer rim of the insert component includes an inferior rim section and a superior rim section that extends at a non-orthogonal angle relative to the inferior rim section.

15. The orthopaedic prosthesis of claim 14, wherein the inferior rim section of the insert component extends parallel to the distal rim of the acetabular shell component.

16. The orthopaedic prosthesis of claim 11, wherein the insert component includes an outer wall that is positioned opposite the inner wall, the outer wall including a lateral edge that is positioned lateral of the imaginary plane.

17. The orthopaedic prosthesis of claim 11, further comprising the femoral prosthetic component including an elongated stem and the femoral head secured to the elongated stem.

18. The orthopaedic prosthesis of claim 17, wherein the femoral head includes a geometric center that is positioned lateral of the imaginary plane of the shell component.

19. The orthopaedic prosthesis of claim 11, wherein, when the orthopaedic prosthesis is viewed in cross-section, the cylindrical surface extends a first distance from the outer rim to an inner end on an inferior side of the insert component and the cylindrical surface extends a second distance from the outer rim to the inner end on a superior side of the insert component, the second distance being less than the first distance.

20. An orthopaedic prosthesis, comprising:
a femoral prosthetic component including an elongated stem and a femoral head secured to the elongated stem,
an acetabular shell component having a distal rim and a concave curved surface extending from the distal rim to define an inner cavity, the distal rim being positioned in an imaginary plane, and
an insert component configured to be received in the inner cavity, the insert component including an outer rim, an inner wall extending inwardly from the outer rim, and a cavity defined by the inner wall, the cavity being sized to receive the femoral head of the femoral prosthetic component,
wherein the femoral head includes a geometric center that is positioned lateral of the imaginary plane of the shell component,
wherein the inner wall includes a cylindrical surface extending inwardly from the outer rim to an inner end, and a semi-spherical surface connected to the inner end of the cylindrical surface, and
wherein the semi-spherical surface extends through the imaginary plane to define a region shaped to resist dislocation of the femoral head from the cavity.

* * * * *